US007056723B2

(12) United States Patent
Heller et al.

(10) Patent No.: US 7,056,723 B2
(45) Date of Patent: Jun. 6, 2006

(54) METHOD FOR THE RECOVERY AND PURIFICATION OF POXVIRUSES FROM INFECTED CELLS

(75) Inventors: Karl Heller, Unterföhring (DE); Jutta Kramer, Olching (DE)

(73) Assignee: Bavarian Nordic A/S, Copenhagen (DK)

( * ) Notice: Subject to any disclaimer, the term of this patent is extended or adjusted under 35 U.S.C. 154(b) by 0 days.

(21) Appl. No.: 10/495,151

(22) PCT Filed: Dec. 13, 2002

(86) PCT No.: PCT/EP02/14179

§ 371 (c)(1), (2), (4) Date: May 10, 2004

(87) PCT Pub. No.: WO03/054175

PCT Pub. Date: Jul. 3, 2003

(65) Prior Publication Data

US 2004/0265986 A1 Dec. 30, 2004

(30) Foreign Application Priority Data

Dec. 20, 2001 (DK) ................................ 2001 01928

(51) Int. Cl.
*C12N 7/02* (2006.01)

(52) U.S. Cl. ...................................................... 435/239

(58) Field of Classification Search ................ 435/239, 435/235.1; 424/199.1, 232.1
See application file for complete search history.

(56) References Cited

U.S. PATENT DOCUMENTS

| | | | | |
|---|---|---|---|---|
| 3,983,008 | A | 9/1976 | Shinozaki et al. | |
| 4,255,521 | A | 3/1981 | Hirohara et al. | |
| 5,380,826 | A | 1/1995 | Castor et al. | |
| 5,721,120 | A | 2/1998 | Seifert et al. | |
| 6,000,551 | A | 12/1999 | Kanel et al. | |
| 6,194,191 | B1 | 2/2001 | Zhang et al. | |
| 2003/0108860 | A1 * | 6/2003 | Reiter et al. | 435/5 |

FOREIGN PATENT DOCUMENTS

| | | |
|---|---|---|
| CH | 621 573 | 8/1976 |
| DE | 199 18 619 | 10/2000 |
| GB | 877 898 | 12/1956 |
| WO | WO 97/02355 | 1/1997 |
| WO | WO 97/12959 | 4/1997 |
| WO | WO 98/13500 | 4/1998 |

OTHER PUBLICATIONS

Gomez et al (Archives of Virology 146:875-892, 2001).*
Balachandran et al (Journal of General Virology 45:65-72, 1979).*
Olsen et al (J. Clin. Micobiol. 6: 50-54, 1977).*
Preparation and Evluation of a Noninfectious Monkey Pox Virus Vaccine by Olsen et al. (Journal of Clinical Microbiology Jul. 1977) 6:50-54.
P.T. Milburn; Biotechnology and Bioengineering; vol. 44; pp. 735-744 (1994); The release of virus-like particles . . .

* cited by examiner

*Primary Examiner*—Mary E. Mosher
(74) *Attorney, Agent, or Firm*—Herbert Dubno

(57) ABSTRACT

The present invention relates to a method for the recovery of poxviruses, in particular modified Vaccinia virus Ankara (MVA), from infected cells. According to the present invention the virus-infected cells are subjected to a high-pressure homogenization to obtain a virus containing homogenate. The virus containing homogenate can be subjected to at least one purification step to obtain apoxvirus-enriched fraction. The invention further relates to the virus containing fraction and the virus containing homogenate obtained by the method according to the present invention.

15 Claims, 1 Drawing Sheet

METHOD FOR THE RECOVERY AND PURIFICATION OF POXVIRUSES FROM INFECTED CELLS

The present invention relates to a method for the recovery of poxviruses, in particular modified Vaccinia virus Ankara (MVA), from infected cells. According to the present invention the poxvirus-infected cells are subjected to a high-pressure homogenization to obtain a poxvirus-containing homogenate. The poxvirus-containing homogenate can be subjected to at least one purification step to obtain a poxvirus-enriched fraction. The invention further relates to the poxvirus-containing fraction and the poxvirus-containing homogenate obtained by the method according to the present invention.

BACKGROUND OF THE INVENTION

The poxviridae comprise a large family of complex DNA viruses that replicate in the cytoplasm of vertebrate and invertebrate cells. The family of poxviridae can be divided into the subfamily chordopoxvirinae (vertebrate poxviruses) and extomopoxvirinae (insect poxviruses).

The chordopoxvirinae comprise several animal poxviruses (classified in different genera) of significant economical importance, such as camelpox viruses, sheeppox virus, goatpox virus or avipoxviruses, in particular fowlpoxvirus. For the vaccination of livestock against sheeppox and goatpox attenuated live-virus and inactivated vaccines are available. For the vaccination of poultry recombinant vaccines have been developed using fowlpox virus as a vector.

Since fowlpoxvirus infects human cells it is assumed that it can also be used as a vector to express heterologous genes in humans and to induce a corresponding immune response. Fowlpoxviruses containing HIV genes in the genome are disclosed in U.S. Pat. Nos. 5,736,368 and 6,051,410.

In humans the variola virus, a member of the genus *Orthopoxvirus*, was by far the most important poxvirus. Vaccinia virus, also a member of the genus *Orthopoxvirus* in the family of poxviridae, was used as live vaccine to immunize against smallpox. Successful worldwide vaccination with Vaccinia virus culminated in the eradication of variola virus (The global eradication of smallpox. Final report of the global commission for the certification of smallpox eradication; History of Public Health, No. 4, Geneva: World Health Organization, 1980). Since that WHO declaration, vaccination has been discontinued for many years except for people at high risk of poxvirus infections (e.g. laboratory workers). Vaccination programs are again becoming of interest in view of the risk that variola virus is used in biological warfare or by bioterrorists.

More recently, Vaccinia viruses have also been used to engineer viral vectors for recombinant gene expression and for the potential use as recombinant live vaccines (Mackett, M., Smith, G. L. and Moss, B. [1982] P.N.A.S. USA 79, 7415–7419; Smith, G. L., Mackett, M. and Moss, B. [1984] Biotechnology and Genetic Engineering Reviews 2, 383–407). This entails DNA sequences (genes), which code for foreign antigens being introduced, with the aid of DNA recombination techniques, into the genome of the Vaccinia viruses. If the gene is integrated at a site in the viral DNA which is non-essential for the life cycle of the virus, it is possible for the newly produced recombinant Vaccinia virus to be infectious, that is to say able to infect foreign cells and thus to express the integrated DNA sequence (EP Patent Applications No. 83, 286 and No. 110, 385). The recombinant Vaccinia viruses prepared in this way can be used, on the one hand, as live vaccines for the prophylaxis of infectious diseases, on the other hand, for the preparation of heterologous proteins in eukaryotic cells.

The use of Vaccinia virus as vector for the development of recombinant live vaccines has been affected by safety concerns and regulations. Most of the recombinant Vaccinia viruses described in the literature are based on the Western Reserve strain of Vaccinia virus. It is known that this strain has a high neurovirulence and is thus poorly suited for use in humans and animals (Morita et al., Vaccine 5, 65–70 [1987]). On the other hand the Modified Vaccinia virus Ankara (MVA) is known to be exceptionally safe. MVA has been generated by longterm serial passages of the Ankara strain of Vaccinia virus (CVA) on chicken embryo fibroblasts (for review see Mayr, A., Hochstein-Mintzel, V. and Stickl, H. [1975] Infection 3, 6–14; Swiss Patent No. 568, 392). Examples for MVA virus strains deposited in compliance with the requirements of the Budapest Treaty are strains MVA 572, MVA 575 and MVA-BN deposited at the European Collection of Animal Cell Cultures (ECACC), Salisbury (UK) with the deposition numbers ECACC V94012707, ECACC V00120707 and ECACC V00083008, respectively. MVA is distinguished by its great attenuation that is to say by diminished virulence or infectiosity while maintaining good immunogenicity. The MVA virus has been analyzed to determine alterations in the genome relative to the wild type CVA strain. Six major deletions of genomic DNA (deletion I, II, III, IV, V, and VI) totaling 31,000 base pairs have been identified (Meyer, H., Sutter, G. and Mayr A. [1991] J. Gen. Virol. 72, 1031–1038). The resulting MVA virus became severely host cell restricted to avian cells. Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr et al., Zbl. Bakt. Hyg. I, Abt. Org. B 167, 375–390 [1987], Stickl et al., Dtsch. med. Wschr. 99, 2386–2392 [1974]). During these studies in over 120,000 humans, including high-risk patients, no side effects were associated with the use of MVA vaccine. Recombinant MVA useful as vaccines have already been constructed and used in clinical trials. WO 98/13500 discloses a recombinant MVA containing and capable of expressing one or more DNA sequences encoding dengue virus antigens. The foreign DNA sequences were recombined into the viral DNA at the site of a naturally occurring deletion in the MVA genome.

Before using poxviruses or recombinant poxvirus for vaccination it is necessary to purify the virus to a certain extent in order to meet regulatory requirements. The traditional way to purify poxviruses, in particular MVA and recombinant MVA is as follows: in a first step cells suscep tible to infection with the respective poxvirus are cultivated. In case of MVA the susceptible cells are i.a. chicken embryo fibroblasts. The susceptible cells are infected with the poxvirus and cultivated for a time period sufficient to allow the generation of virus progeny. The cells then are frozen and thawed in order to detach the cells from the culture vial surface and to partially disrupt the cells. The mixture of intact and disrupted cells is spun down. Ultrasound is used to produce a homogenate. Virus is purified from the homogenate by sucrose cushion centrifugation (Joklik WK. "The purification of four strains of poxvirus" Virology 1962; 18:9–18). The key step in this process is the homogenization by using ultrasound (Hedström, K. G. and Lindberg, U., Z. Immun. Forsch. 1969 137:421–430; Stickl, H., Korb, W. and Hochstein-Mintzel, V., Zbl. Bakt., I. Abt. Orig. (1970), 215, 38–50). In industrial processes it is preferred that all process steps are easy to control and reproducible. However the disadvantage in using ultrasound to homogenize the virus-cell suspension is that the ultrasound step is difficult to reproduce in an identical manner, difficult to adjust and it is difficult to scale up the process from laboratory to industrial scale.

OBJECT OF THE INVENTION

Thus, it is an object of the invention to provide a method for the recovery of poxviruses, in particular of Vaccinia viruses, such as strain MVA, from poxvirus infected cells, wherein the homogenization of the infected cells is reproducible, easy to control and allows an easy scaling up from laboratory to industrial scale.

DETAILED DESCRIPTION OF THE INVENTION

The present invention concerns a method for the recovery of poxviruses, in particular vaccinia viruses, such as strain Elstree or Modified Vaccinia Virus Ankara (MVA), from infected cells. The method according to the present invention for the recovery of poxvirus from infected cells comprises the step of subjecting the infected cells to a high-pressure homogenization to obtain a poxvirus-containing homogenate.

It was unexpected that intact and infectious poxviruses can be recovered by the method according to the present invention. High-pressure homogenization is commonly used for the destruction of cellular and subcellular structures in order to isolate proteins or lipids from eukaryotic and prokaryotic cells. U.S. Pat. No. 3,983,008 discloses a method of extracting useful components from microbial cells by using high pressure homogenizations. The extracted compounds were yeast proteins, bacterial enzymes and yeast lipids. DE 19918619 discloses the use of high-pressure homogenization to isolate HbsAg from yeast cells. U.S. Pat. No. 4,255,521 describes a process for extracting glucose isomerase from microorganism cells by high pressure release. High-pressure homogenization has also been used for the isolation of virus-like particles (VLP) from recombinant *Saccharomyces cerevisiae* (Milburn and Dunnill (1994) Biotechnology and Bioengineering 44, 736–744) and for the production and purification of adenoviral vectors (U.S. Pat. No. 6,194,191). VLPs and Adenoviruses are non-enveloped and rather small and simple viruses that, thus, resemble cellular protein structures. Therefore, it is not astonishing that the high-pressure homogenization that has been shown to be suitable for the isolation of proteins from cells can also be used for the isolation of Adenoviruses and VLPs from eukaryotic cells. In contrast, the intracellular mature poxvirus virions (IMV, see below, see Fields et al., Fields Virology, 1996, Lippincott-Raven publishers, Philadelphia, USA, ISBN 0-7817-0253-4, chapter 83, pages 2654–5) have a very complex morphology that involves inter alia lipid membranes. The morphology and physical properties of a poxvirus IMV are in some aspects more closely related to the morphology and the physical properties of a cell than to those of a non-enveloped virus. Consequently, it was expected that the conditions used for the disruption of cells by using high-pressure homogenization would also lead to the disruption of poxviruses. Thus, it was a surprising result that high-pressure homogenization disrupts cells but leaves intact a sufficient amount of poxviruses that may be further purified. In other words, one would not have assumed that high-pressure homogenization could be used in a method for the recovery of poxviruses from infected cells. Indeed, the known method for the recovery of poxviruses from infected cells uses ultrasound for homogenization, which is a rather gentle way of homogenization.

In contrast to the recovery methods that use ultrasound the method according to the present invention allows a reproducible homogenization of infected cells; the method is easy to control and it is easy to scale up the process from a laboratory to an industrial scale.

In the context of the present invention the term "poxvirus" refers to any virus belonging to the family poxviridae. The method according to the present invention is preferably carried out with poxviridae of the subfamily chordopoxvirinae, more preferably of the genera *orthopoxvirus, avipoxvirus, capripoxvirus* and *suipoxvirus*. Most preferably the invention concerns a method for the recovery and purification of poxviruses selected from the group consisting of Vaccinia virus, goatpoxvirus, sheeppoxvirus, canarypoxvirus and fowlpoxvirus. Particularly preferred is Vaccinia virus. Examples for vaccinia virus strains used in the method according to the present invention are the strains Elstree, Wyeth, Copenhagen, Temple of Heaven, NYCBH, Western Reserve. The invention is not restricted to those specifically mentioned vaccinia virus strains but may instead be used with any vaccinia virus strain. A preferred example for a Vaccinia virus strain is the modified Vaccinia virus strain Ankara (MVA). A typical MVA strain is MVA 575 that has been deposited at the European Collection of Animal Cell Cultures under the deposition number ECACC V00120707. Most preferred is MVA-BN or a derivative thereof. MVA-BN has been described in WO 02/42480 (PCT/EP01/13628). Said international application discloses biological assays allowing to evaluate whether a MVA strain is MVA-BN or a derivative thereof and methods allowing to obtain MVA-BN or a derivative thereof. The content of this application is included in the present application by reference.

MVA-BN has been deposited at the European Collection of Animal Cell Cultures with the deposition number ECACC V00083008.

The viruses to be recovered may be native viruses, attenuated viruses or recombinant viruses.

The term "recombinant virus" refers to any virus having inserted into the viral genome a heterologous gene that is not naturally part of the viral genome. A heterologous gene can be a therapeutic gene, a gene coding for an antigen or a peptide comprising at least one epitope to induce an immune response, an antisense expression cassette or a ribozyme gene. Methods to obtain recombinant viruses are known to a person skilled in the art. The heterologous gene is preferably inserted into a non-essential region of the virus genome. In another preferred embodiment of the invention, the heterologous nucleic acid sequence is inserted at a naturally occurring deletion site of the MVA genome (disclosed in PCT/EP96/02926).

An "attenuated virus" is a virus that upon infection of the host organism results in a lower mortality and/or morbidity compared to the non-attenuated parent virus. An example for an attenuated Vaccinia virus is strain MVA, in particular MVA-575 and MVA-BN.

Poxviruses, such as Vaccinia virus, are known to exist in two different forms: poxvirus attached to cellular membranes in the cytoplasm of the infected cells (intracellular mature virions (IMV)) and viruses that have been externalized (extracellular enveloped virions (EEV)) (Vanderplasschen A, Hollinshead M, Smith G L "Intracellular and extracellular vaccinia virions enter cells by different mechanisms" J. Gen. Virol. (1998), 79, 877–887). IMVs and EEVs are both infectious but morphologically different since EEV contain an additional lipoprotein envelope. Under normal circumstances IMV particles are more abundant than EEV, but in the method according to the invention both types of particles can be obtained.

The starting materials for the homogenization step according to the present invention are cells infected with the respective poxvirus. The term "infected cells" used to define the starting material for the homogenization according to the present invention refers to intact cells infected with the respective virus, to parts and fragments of infected cells to which the respective poxvirus is attached or to a mixture of intact cells and lysed/disrupted cells. Examples for a part or a fragment of infected cells are cell membranes of disrupted/lysed cells to which the respective poxvirus is attached. The starting material may also contain free virus particles that are neither attached to cellular membrane nor located intracellularly.

In order to obtain the infected cells that are the starting material for the method according to the present invention eukaryotic cells are infected with the respective poxvirus. The eukaryotic cells are cells that are susceptible to infection with the respective poxvirus and allow replication and production of infectious virus. Such cells are known to the person skilled in the art for all poxviruses. For MVA and vaccinia virus strain Elstree an example for this type of cells are chicken embryo fibroblasts (CEF) (Drexler I., Heller K., Wahren B., Erfle V. and Sutter G. "Highly attenuated modified vaccinia Ankara replicates in baby hamster kidney cells, a potential host for virus propagation, but not in various human transformed and primary cells" J. Gen. Virol. (1998), 79, 347–352). CEF cells can be cultivated under conditions known to the person skilled in the art. Preferably the CEF cells are cultivated in serum-free medium in stationary flasks or roller bottles. The incubation preferably takes place 48 to 96 hours at 37° C.±2° C. For the infection poxviruses are preferably used at a multiplicity of infection (MOI) of 0,05 to 1 $TCID_{50}$ and the incubation preferably takes place 48 to 72 hours at 37° C.±2° C.

Progress of infection can be observed by looking at cytopathic effects (CPE), typically appearing by significant rounding of the infected cells.

The present invention allows the recovery of poxviruses, such as Elstree or MVA from infected cells. By the term "recovery" it is meant that the method of the present invention allows to disrupt poxvirus infected cells and/or to detach the poxviruses from the cellular membranes to which they are usually bound, to such an extend that a further purification of the poxvirus becomes feasible. Thus, the product of the recovery of poxviruses from infected cells (referred to as "poxvirus-containing homogenate" in the present application) is a homogenous mixture of free poxvirus and cellular detritus containing only minor amounts of intact, undisrupted cells and virus bound to cellular membranes.

If the infected cells are cells that can be cultivated in suspension culture the infected cells can easily be harvested by centrifugation.

If the infected cells are more or less intact adherent cells they should be harvested, i.e. removed from the culture vial, before subjecting them to the high-pressure homogenization. Such methods are known to the person skilled in the art. Useful techniques are mechanic methods (e.g. by using a rubber cell scraper), physical methods (e.g. freezing below −15° C. and thawing the culture vessels above +15° C.) or biochemical methods (treatment with enzymes, e.g. trypsin, to detach the cells from the culture vessel). If enzymes are used for this purpose the incubation time should be controlled, since these enzymes may also damage the virus during incubation.

In the method according to the present invention the infected cells, more specifically the harvested infected cells are then subjected to a high pressure homogenization step. In the present specification the term "high pressure homogenization" is sometimes abbreviated as "HPH". The high-pressure homogenization has a dual effect. On the one hand the high-pressure homogenization leads to the disruption of intact cells. Thus, the IMVs are freed and become available for a further purification. On the other hand the high-pressure homogenization has the effect that the poxviruses are detached from cell membranes or at least that the size of the cell-membrane-virus aggregates is reduced. Again, this simplifies the further purification of the poxvirus.

The person skilled in the art is familiar with the general principle of high-pressure homogenization (White M D, Marcus D., "Disintegration of microorganisms", Adv. Biotechnol. Processes 1988; 8:51–96). HPH Systems are based on the use of high pressure to force a sample through a small fixed orifice at high speed under controlled and repeatable conditions. In the present description the terms "jet", "orifice" and "nozzle" are used interchangeably.

The heart of each cell disrupter is a disruption head. The disruption head preferably consists of (I) a high pressure chamber/cylinder, (II) a high pressure piston which moves into the chamber/cylinder and thereby increases the pressure in the chamber/cylinder and (Ill) a nozzle/jet through which the chamber content is ejected. The ejected chamber content is directed to a target surface such as a piece of metal that preferably has a heat exchange surface allowing cooling. To collect the disrupted chamber content the system is provided with means for collection of the disrupted sample (termed "collection chamber"). A typical high pressure homogenization unit is Basic Z+from Constant Cell Disruption Systems (Low March, Daventry, Northants, NN114SD, United Kingdom).

In a preferred embodiment there are three stages to effect cell disruption using the high-pressure homogenization system. (I) A sample is introduced into the high pressure cylinder/chamber. Then the pressure in the cylinder/chamber is built up. To this end the high pressure piston descends. (II) The piston then forces the sample through the nozzle at high speed. The rapid transfer of the sample from a region of high pressure to one of low pressure causes cell disruption. (III) The sample hits the target and is spread radially across the cooled heat exchange surface. The product then flows into a chamber for collection. The hydraulics is recharged and the cycle continues.

At the end of the process the ejected homogenate is collected in an appropriate vial, depending on the volume.

For the recovery of poxviruses according to the present invention the nozzle should have a diameter in the range of 0.10 to 0.6 mm, 0.15 to 0.6 mm, 0.15 to 0.50 mm, preferably in the range of 0.15 to 0.40 mm, 0.20 to 0.50 mm, more preferably 0.20 to 0.40 mm, most preferably 0.25 mm to 0.35 mm. Examples for most preferred diameters are 0.25 mm and 0.35 mm.

The pressure in the pressure chamber/cylinder is set to a value in the range of 200 to 1000 bar, preferably 400 to 1000 bar, 200 to 800 bar, more preferably 400 to 800 bar, 600 to 1000 bar, even more preferably 600 to 900 bar, most preferably 700 to 900 bar. The most preferred pressure is 800 bar.

The temperature of the homogenate at the outlet preferably should not exceed +25° C., and should preferably be below 15° C., most preferably below 10° C.

The method according to the present invention can be scaled-up almost linear and can be run either as batch or as continuous process.

In a batch process each batch of the cells to be homogenized can be subjected to the high pressure homogenization step once or several times. Preferably each batch is subjected to the homogenization step one to three times, most preferably only once.

The success of the homogenization step may preferably be checked by determination of the virus titer (equivalent to the number of infectious virus particles, measured either in tissue culture infectious dose ($TCID_{50}$), or plaque forming units (pfu)) of the starting material as defined above and of the material obtained after the homogenization step. In other words the virus titer is determined before and after the high-pressure homogenization. The starting material comprises more or less intact cells and a rather high percentage of large aggregates comprising poxvirus particles bound to cellular membranes. If such a material is used for the determination of the viral titer the obtained titer is lower than the actual number of infectious particles. This is due to the fact that the test systems used for the determination of the viral titer are usually cell culture systems (such as the system as disclosed in Example 2) in which the number of infected cells or the number of plaques is counted. Such a system can not distinguish between a positive result that is due to the infection of a cell by just one virus particle and the infection of cells e.g. by a large aggregate of viruses bound to cellular membranes. After the high-pressure homogenization the poxviruses become detached from the cellular membranes and/or the size of cell membrane-virus aggregates is significantly reduced, which leads to a larger number of smaller aggregates. If this material is used for the determination of the titer the obtained results are higher, even if the actual amount of infectious virus particles has not changed. Thus, the success of the homogenization is preferably reflected by at least an equal or higher $TCID_{50}$/ml ("TCID" is the abbreviation of "tissue culture infectious dose") of the homogenate compared to the starting material. In the example section it is shown in detail how the $TCID_{50}$/ml value can be determined. Alternatively, the quality and the success of the high-pressure homogenization can be determined by electron microscopy.

For further purification the obtained homogenate is subjected to at least one purification step to obtain a poxvirus-enriched fraction. In particular, these steps can be carried out for a vaccinia virus containing homogenate if it is intended to further purify said vaccinia virus.

The purification step inter alia can be

- batch centrifugation (e.g. using sucrose cushions) or continuous-flow ultracentrifugation (sucrose gradients) (Hilfenhaus, J., Köhler, R. and Gruschkau, H., J. Biol. Stand. (1976) 4, 285–293; Madalinski, W., Bankovski, A. and Korbecki, M., Acta Virol. (1977) 21, 104–108),
- ultrafiltration (e.g. cross-flow filtration using a membrane with a pore size bigger than 500 kDa, but equal or smaller than 0,1 μm),
- column chromatography (e.g. ion exchange, hydrophobic interaction, size exclusion or a combination) (Hedström, K. G. and Lindberg, U., Z. Immun. Forsch. 1969 137:421–430; Stickl, H., Korb, W. and Hochstein-Mintzel, V., Zbl. Bakt., I. Abt. Orig. (1970), 215, 38–50) or
- a combination of all of the above (Masuda, N., Ellen, R. P. and Grove, D. A., J. Bacteriol. (1981), 147(3), 1095–1104).

Any other purification methods known to the person skilled in the art are also within the scope of the present invention.

Preferably the purification step is an ultrafiltration step. Most preferably the ultrafiltration is a cross-flow filtration. The principle of cross-flow filtration is known to the person skilled in the art. See, e.g., Richards, G. P. and Goldmintz, D., J. Virol. Methods (1982), 4(3), pages 147–153. "Evaluation of a cross-flow filtration technique for extraction of polioviruses from inoculated oyster tissue homogenates".

Although one purification step might be sufficient to meet regulatory requirements for biopharmaceutical products, two or more of the above mentioned purification steps can be combined in order to obtain an even more pure product.

In the most preferred embodiment the first purification step is a cross-flow-filtration followed by at least one column chromatography step. Most preferably the column chromatography step is ion exchange or hydrophobic interaction.

The obtained virus enriched fraction is optionally freeze-dried. Methods of freeze-drying are known to the person skilled in the art (Day J. and McLellan M., Methods in Molecular Biology (1995), 38, Humana Press, "Cryopreservation and freeze-drying protocols").

The invention further concerns the poxvirus-enriched fraction and/or the poxvirus-containing homogenate obtained by the method for recovery of poxviruses according to the present invention, i.e. the method that comprises the step of subjecting the infected cells to high-pressure homogenization. In particular the invention concerns the poxvirus-enriched fraction obtained by the recovery/purification method according to the present invention, i.e. the method in which the poxvirus-containing homogenate obtained by HPH is subjected to at least one purification step. The poxvirus may be any poxvirus as defined above. In particular the poxvirus according to the present invention is a vaccinia virus as, such any strains that are suitable for vaccination, in particular strain Elstree or modified vaccinia virus Ankara, most preferably MVA-BN.

The poxvirus containing homogenate and/or the poxvirus-enriched fraction obtained by a process according to the present invention that comprises a HPH step is characterized by a very high free-IMV poxvirus to EEV poxvirus ratio. The term "free IMV" is used for IMVs that have been detached from the cellular membranes after, before or during disruption of the infected cells and that therefore can be further purified. In all industrial processes for the preparation of poxviruses the starting material comprises the infected cells as well as the culture supernatant. Thus, the starting material comprises IMV poxviruses contained in the infected cells as well as EEV poxviruses which are mainly found in the supernatant. The known methods for the disruption of cells and the subsequent homogenization (e.g. by using ultrasound) do not as efficiently disrupt the cells and/or detach the IMV poxviruses from cellular debris as high pressure homogenization. In other words most of the IMV remain bound to cellular membranes and debris. Thus, the ratio of free IMV to EEV is lower than in the method according to the present invention. In the method using ultrasound this ratio does not change significantly during the further purification steps since the cellular debris to which IMVs are still bound is usually removed. In contrast to the known recovery methods for poxviruses the recovery method according to the present invention results in a very effective disruption of the infected cells and the IMVs are very effectively detached from the cell membranes. Thus, the overall amount of free IMVs that become available for further purification is higher than for the methods known in the prior art and consequently also the ratio of free IMV to EEV poxviruses is higher.

The poxvirus-containing homogenate and/or the poxvirus-enriched fraction obtained by the method according to the present invention are useful as vaccines.

If the poxvirus-containing homogenate and/or the poxvirus-enriched fraction comprise unmodified poxviruses or attenuated poxviruses, such as vaccinia virus strains Elstree or MVA, it can be used for vaccination against poxvirus infections. E.g. a virus containing homogenate and/or the virus-enriched fraction that comprises vaccinia viruses such as strain Elstree or MVA, in particular MVA-BN can be used as a vaccine against smallpox infections.

If the poxvirus-containing homogenate and/or the poxvirus-enriched fraction comprises a poxvirus that contains and expresses one or more heterologous gene(s) the poxvirus-containing homogenate and/or the poxvirus-enriched fraction can further be used to vaccinate animals including human beings against the protein expressed by the heterologous gene(s).

For the preparation of a vaccine, the poxvirus-containing homogenate and/or the poxvirus-enriched fraction obtained by the method according to the present invention are converted into a physiologically acceptable form. This can be done based on the experience in the preparation of poxvirus vaccines used for vaccination against smallpox (as described by Stickl, H. et al. [1974] Dtsch. med. Wschr. 99, 2386–2392). For example, the poxvirus-containing homogenate and/or the poxvirus-enriched fraction are stored at −80° C. with a titer of $5\times10^8$ $TCID_{50}$/ml formulated in about 10 mM Tris, 140 mM NaCl pH 7.4. For the preparation of vaccine shots, e.g., $10^3$–$10^9$ $TCID_{50}$ of the virus are lyophilized in phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. A typical virus containing formulation suitable for freeze-drying comprises 10 mM Tris-buffer, 140 mM NaCl, 18.9 g/l Dextran (MW 36000–40000), 45 g/l Sucrose, 0.108 g/l L-glutamic acid mono potassium salt monohydrate pH 7.4. The glass ampoule is then sealed and can be stored between 4° C. and room temperature for several months. However, as long as no need exists the ampoule is stored preferably at temperatures below −20° C.

For vaccination the lyophilized or freeze-dried product can be dissolved in 0.1 to 0.5 ml of an aqueous solution, preferably physiological saline or Tris buffer, and administered either systemically or locally, i.e. parenterally, intramuscularly or by any other path of administration know to the skilled practitioner. The mode of administration, the dose and the number of administrations can be optimized by those skilled in the art in a known manner. Most preferred for poxvirus vectors is subcutaneous or intramuscular administration.

The invention further relates to a method for the vaccination of animals including humans comprising inoculating an animal, including a human, in need thereof with a poxvirus-containing homogenate or a poxvirus-enriched fraction obtained by the method according to the present invention.

SUMMARY OF THE INVENTION

The invention inter alia comprises the following, alone or in combination:

Method for the recovery of poxvirus from infected cells comprising the step of subjecting the infected cells to a high-pressure homogenization to obtain a poxvirus-containing homogenate.

Method as above characterized in that the poxvirus is selected from the group consisting of *orthopoxviruses, avipoxviruses, suipoxviruses* and *capripoxviruses*

Method as above characterized in that the poxvirus is selected from the group consisting of vaccinia virus, goatpoxvirus, sheeppoxvirus, canarypoxvirus and fowlpoxvirus Method as above characterized in that the vaccinia virus is modified vaccinia virus strain Ankara (MVA), in particular MVA-BN with the deposition number ECACC V00083008.

Method as above characterized in that the poxvirus is a recombinant pox virus.

Method as above characterized in that the high-pressure homogenization is carried out by putting the infected cells into a high pressure chamber, increasing the pressure in the chamber and ejecting the infected cells through a nozzle.

Method as above characterized in that the pressure in the chamber is increased to a value in the range of 200 to 1000 bar.

Method as above characterized in that the nozzle has a diameter in the range of 0.10 to 0.6 mm.

Method as above characterized in that the poxvirus-containing homogenate is subjected to at least one purification step to obtain a poxvirus-enriched fraction.

Method as above characterized in that the at least one purification step is an ultrafiltration step.

Method as above characterized in that the ultrafiltration is a cross-flow-filtration.

Method as above characterized in that in the cross-flow-filtration step a membrane is used that has a pore size bigger than 500 kDa but equal or smaller than 0.1 μm.

Method as above characterized in that subsequent to the ultrafiltration at least one column chromatography step is carried out Method as above characterized in that the obtained poxvirus-containing homogenate or poxvirus-enriched fraction is freeze-dried Poxvirus-containing homogenate or poxvirus-enriched fraction obtained by a method as defined above.

Poxvirus-containing homogenate or poxvirus-enriched fraction as above as vaccine.

Use of the poxvirus-containing homogenate or poxvirus-enriched fraction as above for the preparation of a vaccine.

Method for the vaccination of an animal, including a human, in need thereof characterized by the administration of a poxvirus-containing homogenate or poxvirus-enriched fraction or a vaccine as defined above to the animal body.

EXAMPLE(S)

Figure 1:
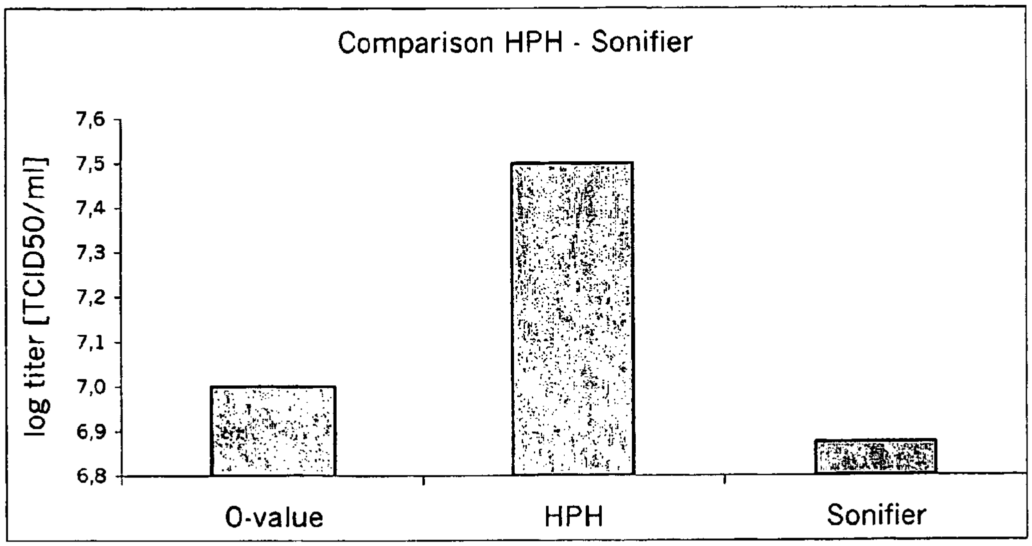
FIG. 1: CEF cells infected with MVA-BN were subjected to a freezing-thawing cycle to obtain a virus-cell suspension. The virus titer of the suspension was determined as described in example 2 without further purification of the cell-virus-suspension ("O-value"). The virus-cell-suspension was subjected to a homogenization method known from the prior art by using ultrasound ("Sonifier") or to the homogenization method according to the present invention ("HPH") as described in Example 1. In the HPH step the pressure was 800 bar and the nozzle had a diameter of 0.25 mm. At the end of the homogenization step the virus titer was again determined.

The following example(s) will further illustrate the present invention. It will be well understood by a person skilled in the art that the provided example(s) in no way may be interpreted in a way that limits the applicability of the technology provided by the present invention to this example(s).

Example 1

Homogenization of Poxvirus-cell-suspensions by Using a High Pressure Homogenizer Chicken embryo fibroblasts (CEF) cultivated in roller flasks have been infected with MVA-BN (ECACC V00083008). The infected cells were subjected to freezing and thawing to obtain a virus-cell-suspension.

A Basic Z+ homogenizer from Constant Cell Disruption Systems (Low March, Daventry, Northants, NN114SD, United Kingdom) was loaded with 50 ml of the crude virus-cell-suspension for each run. In order to identify the optimal homogenization conditions nozzle diameters in the range of 0.18 to 0.40 mm and pressures in the range of 200 to 1000 bar were tested. The crude suspension was subjected to the high pressure homogenization one, two or three times. The homogenizer was used according to the instructions of the manufacturer. The evaluation of the method was executed by monitoring the titer as described in example 2.

In preliminary studies it was found that jet diameters larger than 0.4 mm have no positive influence on the homogenization results. With the nozzle diameters of 0.18 mm, 0.25 mm and 0.35 mm the best results were obtained by subjecting the viruscell suspension once to a pressure of 800 bar. At these conditions no major difference in terms of titer have been observed.

The method according to the present invention was compared to the direct flow-through ultrasound treatment known from the prior art. The results are summarized in FIG. 1. Compared to the ultrasound treatment the method according to the present invention resulted in a higher virus titer and a better homogeneity of the suspension, so that it is more suitable for further downstream processing.

Example 2

Titration of Modified Vaccinia Virus Ankara (MVA)

The titration of Modified Vaccinia virus Ankara (MVA) is performed in a $TCID_{50}$-based assay using 10-fold dilutions in a 96-well format. At the endpoint of the assay, infected cells are visualised using an anti-vaccinia virus antibody and an appropriate staining solution.

2–3 day old primary CEF (chicken embryo fibroblasts) cells are diluted to $1\times10^5$ cells/ml in 7% RPMI. 10 fold dilutions are done with 8 replicates per dilution. Following dilution, 100 μl are seeded per well of 96-well plates. Cells are then incubated over night at 37° C. and 5% $CO_2$.

Dilutions of the virus containing solutions are made in 10-fold steps ($10^{-1}$ to $10^{-12}$ as appropriate) using RPMI without fetal calf serum. Then, 100 μl of every virus sample is added to the cell containing wells.

The 96-well-plates are incubated at 37° C. with 5% $CO_2$ for 5 days to allow infection and viral replication.

Cells are stained 5 days after infection with a vaccinia virus specific antibody. For the detection of the specific antibody, a horseradish peroxidase (HRP) coupled secondary antibody is used. The MVA specific antibody is an anti-vaccinia virus antibody, rabbit polyclonal, IgG fraction (Quartett, Berlin, Germany #9503-2057). The secondary antibody is anti-rabbit IgG antibody, HRP coupled goat polyclonal (Promega, Mannheim, Germany, #W4011). The colour reaction is carried out according to known techniques.

Every well with cells that are positive in the colour reaction is marked as positive for the calculation of the $TCID_{50}$.

The titre is calculated by using the formula of Spearman [1] and Kaerber [2]. Because all assay parameters are kept constant, the following simplified formula is used:

$$\text{Virus titre } [TCID_{50}/\text{ml}] = 10^{[a+1,5+\frac{x_a}{8}+\frac{x_b}{8}+\frac{x_c}{8}]}$$

a=dilution factor of last column, in which all eight wells are positive $x_a$=number of positive wells in column a+1

$x_b$=number of positive wells in column a+2

$x_c$=number of positive wells in column a+3

The invention claimed is:

1. Method for the recovery of poxvirus from infected cells comprising the step of subjecting the infected cells to a high-pressure homogenization to obtain a poxvirus-containing homogenate.

2. Method according to claim 1 characterized in that the poxvirus is selected from the group consisting of *orthopoxviruses, avipoxviruses, suipoxviruses* and *capripoxviruses.*

3. Method according to claim 1 characterized in that the poxvirus is selected from the group consisting of vaccinia virus, goatpoxvirus, sheeppoxvirus, canarypoxvirus and fowlpoxvirus.

4. Method according to claim 3 characterized in that the vaccinia virus is Elstree or modified vaccinia virus strain Ankara (MVA).

5. Method according to claim 1 characterized in that the poxvirus is a recombinant poxvirus.

6. Method according to claim 1 characterized in that the high-pressure homogenization is carried out by putting the infected cells into a high pressure chamber, increasing the pressure in the chamber and ejecting the infected cells through a nozzle.

7. Method according to claim 6 characterized in that the pressure in the chamber is increased to a value in the range of 200 to 1000 bar.

8. Method according to claim 6 characterized in that the nozzle has a diameter in the range of 0.10 to 0.6 mm.

9. Method according to claim 1 characterized in that the poxvirus-enriched containing homogenate is subjected to at least one purification step to obtain a poxvirus-enriched fraction.

10. Method according to claim 9 characterized in that one of the at least one purification steps is an ultrafiltration step.

11. Method according to claim 10 characterized in that the ultrafiltration is a cross-flow-filtration.

12. Method according to claim 11 characterized in that in the cross-flow-filtration step a membrane is used that has a pore size bigger than 500 kDa but equal or smaller than 0.1 gm.

13. Method according to claim 10 characterized in that subsequent to the ultrafiltration at least one column chromatography step is carried out.

14. Method according to claim 1 characterized in the poxvirus-containing homogenate or the poxvirus-enriched fraction is freeze-dried.

15. Method according to claim 4 wherein the modified vaccinia virus Ankara (MVA) is MVA-BN with the deposition number ECACC V00083008.

* * * * *